(12) United States Patent
Springer et al.

(10) Patent No.: US 10,441,645 B2
(45) Date of Patent: Oct. 15, 2019

(54) MSLN TARGETING DNA VACCINE FOR CANCER IMMUNOTHERAPY

(71) Applicant: VAXIMM GMBH, Mannheim (DE)

(72) Inventors: Marco Springer, Wendlingen (DE); Heinz Lubenau, Neustadt an der Weinstrasse (DE)

(73) Assignee: VAXIMM GMBH (DE)

( * ) Notice: Subject to any disclaimer, the term of this patent is extended or adjusted under 35 U.S.C. 154(b) by 0 days.

(21) Appl. No.: 15/785,743

(22) Filed: Oct. 17, 2017

(65) Prior Publication Data
US 2018/0064794 A1    Mar. 8, 2018

Related U.S. Application Data

(63) Continuation of application No. 15/105,739, filed as application No. PCT/EP2014/003403 on Dec. 17, 2014, now abandoned.

(30) Foreign Application Priority Data

Dec. 18, 2013 (EP) ..................................... 13005896

(51) Int. Cl.
| | | |
|---|---|---|
| A61K 39/112 | (2006.01) | |
| A61K 39/205 | (2006.01) | |
| A61K 39/00 | (2006.01) | |
| C12N 1/20 | (2006.01) | |
| C12N 1/36 | (2006.01) | |
| C12R 1/42 | (2006.01) | |

(52) U.S. Cl.
CPC ............ *A61K 39/0011* (2013.01); *C12N 1/20* (2013.01); *C12N 1/36* (2013.01); *C12R 1/42* (2013.01); *A61K 2039/522* (2013.01); *A61K 2039/523* (2013.01); *A61K 2039/53* (2013.01); *A61K 2039/542* (2013.01); *Y02A 50/484* (2018.01)

(58) Field of Classification Search
CPC ........................... A61K 39/00; A61K 39/0275
USPC .................... 424/184.1, 185.1, 234.1, 258.1
See application file for complete search history.

(56) References Cited

U.S. PATENT DOCUMENTS

| 5,726,288 A | 3/1998 | Call et al. |
|---|---|---|
| 9,920,297 B2 | 3/2018 | Lubenau et al. |
| 2006/0068469 A1 | 3/2006 | Payne et al. |
| 2007/0092968 A1 | 4/2007 | Ji et al. |
| 2007/0207170 A1* | 9/2007 | Dubensky ............ C07K 14/195 424/234.1 |
| 2012/0076752 A1 | 3/2012 | Wu et al. |
| 2016/0317634 A1 | 11/2016 | Springer et al. |

FOREIGN PATENT DOCUMENTS

| CN | 1859851 A * | 8/2006 |
|---|---|---|
| WO | WO 2012/149364 | 11/2012 |
| WO | WO 2014/043637 | 3/2014 |

OTHER PUBLICATIONS

Bolhassani et al. "Therapeutic live vaccines as a potential anticancer strategy", International Jounral of Cancer, vol. 131, No. 8, Oct. 15, 2012, pp. 1733-1743, XP055079654.
Chen "User guide pVAX1™—Catalog No. V260-20", Invitrogen by Life Technologies Corporation, Mar. 2, 2012, pp. i-16, XP002713155.
Hotz et al. "Improvement of the live vaccine strain *Salmonella enterica* serovar Typhi Ty21a for antigen delivery via the hemolysin secretion system of *Escherichia coli*", International Journal of Medical Microbiology, Urban Und Fischer, DE, vol. 299, No. 2, Feb. 1, 2009 (Feb. 1, 2009), pp. 109-119.
Le et al. "A Live-Attenuated Listeria Vaccine (ANZ-100) and a Live-Attenuated Listeria Vaccine Expressing Mesothelin (CRS-207) for Advanced Cancers: Phase I Studies of Safety and Immune Induction", Clinical Cancer Research, vol. 18, No. 3, Feb. 1, 2012 (Feb. 1, 2012), pp. 858-868.
Niethammer et al. "A DNA vaccine against VEGF receptor 2 prevents effective angiogenesis and inhibits tumor growth", Nature Medicine, vol. 8, No. 12, 2002, p. 1369-1375, XP002968984.
Niethammer et al. "Double-blind, placebo-controlled first in human study to investigate an oral vaccine aimed to elicit an immune reaction against the VEGF-Receptor 2 in patients with stage IV and locally advanced pancreatic cancer", BMC Cancer, vol. 12, Aug. 20, 2012, pp. 361-368, XP002692736.
Oka et al. "Induction of WT1 (Wilms' tumor gene)-specific cytotoxic T lymphocytes by WT1 peptide vaccine and the resultant cancer regression", Proceedings of the National Academy of Sciences—PNAS,National Academy of Sciences, US, vol. 101, No. 38, Sep. 21, 2004, pp. 13885-13890, XP002391406.
Osada et al. "Induction of Wilms' Tumor Protein (WT1)-Specific Antitumor Immunity Using a Truncated WT1-Expressing Adenovirus Vaccine", Clinical Cancer Research, vol. 15, No. 8, Apr. 1, 2009, pp. 2789-2796, XP055079390.
Shahabi et al. "Live, attenuated strains of Listeria and *Salmonella* as vaccine vectors in cancer treatment", Bioengineered Bugs, vol. 1, No. 4, Jan. 1, 2010, pp. 235-239, XP055079663.
Nishikawa et al. "In vivo antigen delivery by a *Salmonella typhimurium* type III secretion system for therapeutic cancer vaccines", Journal of Clinical Investigation, vol. 116, No. 7, Jul. 1, 2006, pp. 1946-1954, XP002415290.
International Search Report and Written Opinion prepared by the European Patent Office dated Mar. 11, 2015, for International Application No. PCT/EP2014/003403.
Official Action for U.S. Appl. No. 15/105,739, dated Jun. 21, 2017 15 pages.

* cited by examiner

*Primary Examiner* — Rodney P Swartz
(74) *Attorney, Agent, or Firm* — Sheridan Ross P.C.

(57) ABSTRACT

The present invention relates to an attenuated mutant strain of *Salmonella* comprising a recombinant DNA molecule encoding Mesothelin. In particular, the present invention relates to the use of said attenuated mutant strain of *Salmonella* in cancer immunotherapy.

12 Claims, 11 Drawing Sheets

Figure 3:
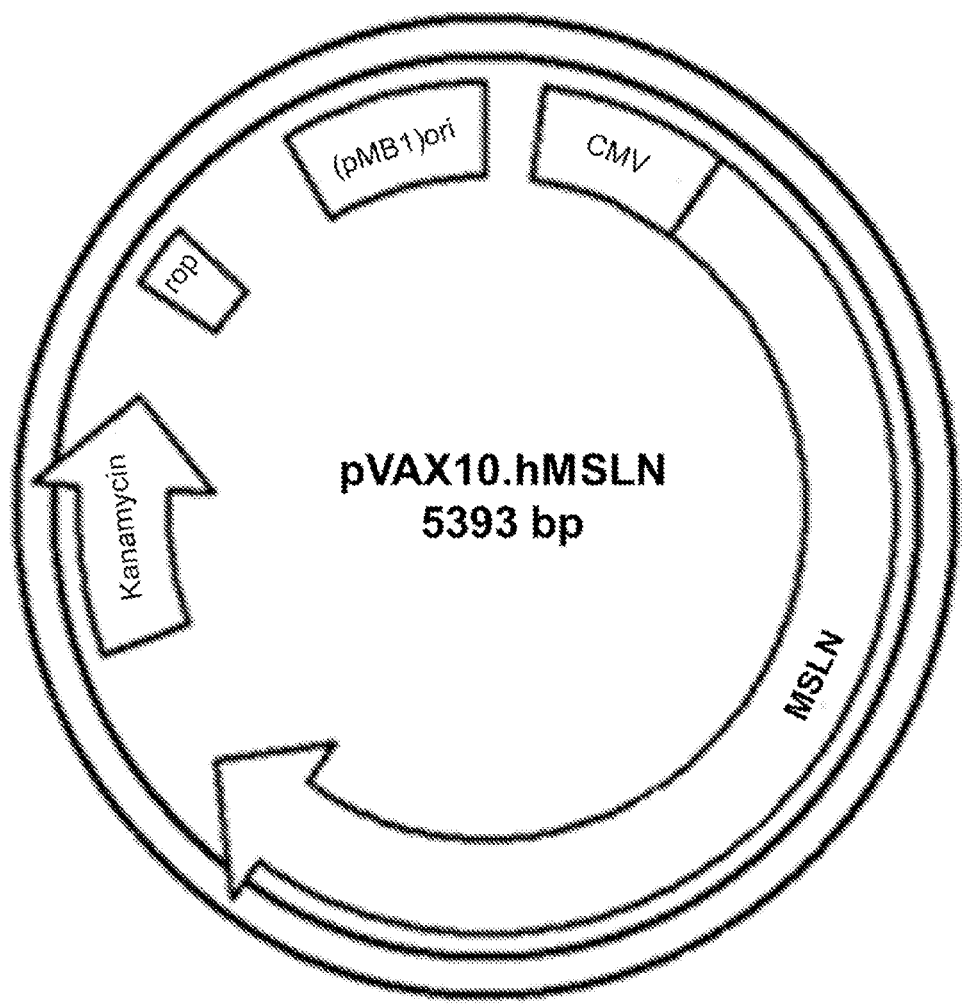

Specification includes a Sequence Listing.

Figure 1:

MALPTARPLLGSCGTPALGSLLFLLFSLGWVQPSRTLAGETGQEAAPLDGVLANPP
NISSLSPRQLLGFPCAEVSGLSTERVRELAVALAQKNVKLSTEQLRCLAHRLSEPPE
DLDALPLDLLLFLNPDAFSGPQACTRFFSRITKANVDLLPRGAPERQRLLPAALACW
GVRGSLLSEADVRALGGLACDLPGRFVAESAEVLLPRLVSCPGPLDQDQQEAARA
ALQGGGPPYGPPSTWSVSTMDALRGLLPVLGQPIIRSIPQGIVAAWRQRSSRDPSW
RQPERTILRPRFRREVEKTACPSGKKAREIDESLIFYKKWELEACVDAALLATQMDR
VNAIPFTYEQLDVLKHKLDELYPQGYPESVIQHLGYLFLKMSPEDIRKWNVTSLETLK
ALLEVNKGHEMSPQAPRRPLPQVATLIDRFVKGRGQLDKDTLDTLTAFYPGYLCSL
SPEELSSVPPSSIWAVRPQDLDTCDPRQLDVLYPKARLAFQNMNGSEYFVKIQSFL
GGAPTEDLKALSQQNVSMDLATFMKLRTDAVLPLTVAEVQKLLGPHVEGLKAEERH
RPVRDWILRQRQDDLDTLGLGLQGGIPNGYLVLDLSMQEALSGTPCLLGPGPVLTV
LALLLASTLA

Figure 2:

TGGGCTTTTGCTGGCCTTTTGCTCACATGTTCTTGACTCTTCGCGATGTACGGG
CCAGATATACGCGTTGACATTGATTATTGACTAGTTATTAATAGTAATCAATTACG
GGGTCATTAGTTCATAGCCCATATATGGAGTTCCGCGTTACATAACTTACGGTAA
ATGGCCCGCCTGGCTGACCGCCCAACGACCCCCGCCCATTGACGTCAATAATG
ACGTATGTTCCCATAGTAACGCCAATAGGGACTTTCCATTGACGTCAATGGGTG
GACTATTTACGGTAAACTGCCCACTTGGCAGTACATCAAGTGTATCATATGCCAA
GTACGCCCCCTATTGACGTCAATGACGGTAAATGGCCCGCCTGGCATTATGCCC
AGTACATGACCTTATGGGACTTTCCTACTTGGCAGTACATCTACGTATTAGTCAT
CGCTATTACCATGGTGATGCGGTTTTGGCAGTACATCAATGGGCGTGGATAGCG
GTTTGACTCACGGGGATTTCCAAGTCTCCACCCCATTGACGTCAATGGGAGTTT
GTTTTGGCACCAAAATCAACGGGACTTTCCAAAATGTCGTAACAACTCCGCCCC
ATTGACGCAAATGGGCGGTAGGCGTGTACGGTGGGAGGTCTATATAAGCAGAG
CTCTCTGGCTAACTAGAGAACCCACTGCTTACTGGCTTATCGAAATTAATACGAC
TCACTATAGGGAGACCCAAGCTGGCTAGCATGGCCTTGCCAACGGCTCGACCC
CTGTTGGGGTCCTGTGGGACCCCGCCCTCGGCAGCCTCCTGTTCCTGCTCTT
CAGCCTCGGATGGGTGCAGCCCTCCAGGACCCTGGCTGGAGAGACAGGGCAG
GAGGCTGCGCCCCTGGACGGAGTCCTGGCCAACCCACCTAACATTTCCAGCCT
CTCCCCTCGCCAACTCCTTGGCTTCCCGTGTGCGGAGGTGTCCGGCCTGAGCA
CGGAGCGTGTCCGGGAGCTGGCTGTGGCCTTGGCACAGAAGAATGTCAAGCTC
TCAACAGAGCAGCTGCGCTGTCTGGCTCACCGGCTCTCTGAGCCCCCCGAGGA
CCTGGACGCCCTCCCATTGGACCTGCTGCTATTCCTCAACCCAGATGCGTTCTC
GGGGCCCCAGGCCTGCACCCGTTTCTTCTCCCGCATCACGAAGGCCAATGTGG
ACCTGCTCCCGAGGGGGGCTCCCGAGCGACAGCGGCTGCTGCCTGCGGCTCT
GGCCTGCTGGGGTGTGCGGGGGTCTCTGCTGAGCGAGGCTGATGTGCGGGCT
CTGGGAGGCCTGGCTTGCGACCTGCCTGGGCGCTTTGTGGCCGAGTCGGCCG
AAGTGCTGCTACCCCGGCTGGTGAGCTGCCCGGGACCCCTGGACCAGGACCA
ACAGGAGGCAGCCAGGGCGGCTCTGCAGGGCGGGGGACCCCCCTACGGCCC
CCCGTCGACATGGTCTGTCTCCACGATGGACGCTCTGCGGGGCCTGCTGCCCG
TGCTGGGCCAGCCCATCATCCGCAGCATCCGCAGGGCATCGTGGCCGCGTG
GCGGCAACGCTCCTCTCGGGACCCATCCTGGCGGCAGCCTGAACGGACCATC
CTCCGGCCGCGGTTCCGGCGGGAAGTGGAGAAGACAGCCTGTCCTTCAGGCA
AGAAGGCCCGCGAGATAGACGAGAGCCTCATCTTCTACAAGAAGTGGGAGCTG
GAAGCCTGCGTGGATGCGGCCCTGCTGGCCACCCAGATGGACCGCGTGAACG
CCATCCCCTTCACCTACGAGCAGCTGGACGTCCTAAAGCATAAACTGGATGAGC
TCTACCCACAAGGTTACCCCGAGTCTGTGATCCAGCACCTGGGCTACCTCTTCC
TCAAGATGAGCCCTGAGGACATTCGCAAGTGGAATGTGACGTCCTGGAGACC
CTGAAGGCTTTGCTTGAAGTCAACAAAGGGCACGAAATGAGTCCTCAGGCTCCT
CGGCGGCCCCTCCCACAGGTGGCCACCCTGATCGACCGCTTTGTGAAGGGAA
GGGGCCAGCTAGACAAAGACACCCTAGACACCCTGACCGCCTTCTACCCTGGG
TACCTGTGCTCCCTCAGCCCCGAGGAGCTGAGCTCCGTGCCCCCAGCAGCAT
CTGGGCGGTCAGGCCCCAGGACCTGGACACGTGTGACCCAAGGCAGCTGGAC
GTCCTCTATCCCAAGGCCCGCCTTGCTTTCCAGAACATGAACGGGTCCGAATAC
TTCGTGAAGATCCAGTCCTTCCTGGGTGGGGCCCCACGGAGGATTTGAAGGC
GCTCAGTCAGCAGAATGTGAGCATGGACTTGGCCACGTTCATGAAGCTGCGGA
CGGATGCGGTGCTGCCGTTGACTGTGGCTGAGGTGCAGAAACTTCTGGGACCC
CACGTGGAGGGCCTGAAGGCGGAGGAGCGGCACCGCCCGGTGCGGGACTGG
ATCCTACGGCAGCGGCAGGACGACCTGGACACGCTGGGGCTGGGCTACAGG
GCGGCATCCCCAACGGCTACCTGGTCCTAGACCTCAGCATGCAAGAGGCCCTC
TCGGGGACGCCCTGCCTCCTAGGACCTGGACCTGTTCTCACCGTCCTGGCACT

Figure 2 Cont.

```
GCTCCTAGCCTCCACCCTGGCCTGACTCGAGTCTAGAGGGCCCGTTTAAACCC
GCTGATCAGCCTCGACTGTGCCTTCTAGTTGCCAGCCATCTGTTGTTTGCCCCT
CCCCCGTGCCTTCCTTGACCCTGGAAGGTGCCACTCCCACTGTCCTTTCCTAAT
AAAATGAGGAAATTGCATCGCATTGTCTGAGTAGGTGTCATTCTATTCTGGGGG
GTGGGGTGGGGCAGGACAGCAAGGGGGAGGATTGGGAAGACAATAGCAGGCA
TGCTGGGGATGCGGTGGGCTCTATGGCTTCTACTGGGCGGTTTATGGACAGC
AAGCGAACCGGAATTGCCAGCTGGGGCGCCCTCTGGTAAGGTTGGGAAGCCCT
GCAAAGTAAACTGGATGGCTTTCTCGCCGCCAAGGATCTGATGGCGCAGGGGA
TCAAGCTCTGATCAAGAGACAGGATGAGGATCGTTTCGCATGATTGAACAAGAT
GGATTGCACGCAGGTTCTCCGGCCGCTTGGGTGGAGAGGCTATTCGGCTATGA
CTGGGCACAACAGACAATCGGCTGCTCTGATGCCGCCGTGTTCCGGCTGTCAG
CGCAGGGGCGCCCGGTTCTTTTTGTCAAGACCGACCTGTCCGGTGCCCTGAAT
GAACTGCAAGACGAGGCAGCGCGGCTATCGTGGCTGGCCACGACGGGCGTTC
CTTGCGCAGCTGTGCTCGACGTTGTCACTGAAGCGGGAAGGGACTGGCTGCTA
TTGGGCGAAGTGCCGGGGCAGGATCTCCTGTCATCTCACCTTGCTCCTGCCGA
GAAAGTATCCATCATGGCTGATGCAATGCGGCGGCTGCATACGCTTGATCCGG
CTACCTGCCCATTCGACCACCAAGCGAAACATCGCATCGAGCGAGCACGTACT
CGGATGGAAGCCGGTCTTGTCGATCAGGATGATCTGGACGAAGAGCATCAGGG
GCTCGCGCCAGCCGAACTGTTCGCCAGGCTCAAGGCGAGCATGCCCGACGGC
GAGGATCTCGTCGTGACCCATGGCGATGCCTGCTTGCCGAATATCATGGTGGA
AAATGGCCGCTTTTCTGGATTCATCGACTGTGGCCGGCTGGGTGTGGCGGACC
GCTATCAGGACATAGCGTTGGCTACCCGTGATATTGCTGAAGAGCTTGGCGGC
GAATGGGCTGACCGCTTCCTCGTGCTTTACGGTATCGCCGCTCCCGATTCGCA
GCGCATCGCCTTCTATCGCCTTCTTGACGAGTTCTTCTGAATTATTAACGCTTAC
AATTTCCTGATGCGGTATTTTCTCCTTACGCATCTGTGCGGTATTTCACACCGCA
TACAGGTGGCACTTTTCGGGGAAATGTGCGCGGAACCCCTATTTGTTTATTTTTC
TAAATACATTCAAATATGTATCCGCTCATGAGACAATAACCCTGATAAATGCTTCA
ATAATAGCACGTGCTAAAACTTCATTTTTAATTTAAAAGGATCTAGGTGAAGATCC
TTTTTGATAATCTCATGACCAAAATCCCTTAACGTGAGTTTTCGTTCCACTGAGC
GTCAGACCCCCATCAGTGACCAAACAGGAAAAAACCGCCCTTAACATGGCCCG
CTTTATCAGAAGCCAGACATTAACGCTTCTGGAGAAACTCAACGAGCTGGACGC
GGATGAACAGGCAGACATCTGTGAATCGCTTCACGACCACGCTGATGAGCTTTA
CCGCAGCTGCCTCGCGCGTTTCGGTGATGACGGTGAAAACCTCTGACACATGC
AGCTCCCGGAGACGGTCACAGCTTGTCTGTAAGCGGATGCCGGGAGCAGACAA
GCCCGTCAGGGCGCGTCAGCGGGTGTTGGCGGGTGTCGGGGCGCAGCCATGA
CCCAGTCACGTAGCGATAGCGGAGTGTATACTGGCTTAACTATGCGGCATCAGA
GCAGATTGTACTGAGAGTGCACCATATGCGGTGTGAAATACCGCACAGATGCGT
AAGGAGAAAATACCGCATCAGGCGCTCTTCCGCTTCCTCGCTCACTGACTCGCT
GCGCTCGGTCGTTCGGCTGCGGCGAGCGGTATCAGCTCACTCAAAGGCGGTAA
TACGGTTATCCACAGAATCAGGGGATAACGCAGGAAAGAACATGTGAGCAAAAG
GCCAGCAAAAGGCCAGGAACCGTAAAAAGGCCGCGTTGCTGGCGTTTTCCAT
AGGCTCCGCCCCCTGACGAGCATCACAAAAATCGACGCTCAAGTCAGAGGTG
GCGAAACCCGACAGGACTATAAAGATACCAGGCGTTTCCCCCTGGAAGCTCCC
TCGTGCGCTCTCCTGTTCCGACCCTGCCGCTTACCGGATACCTGTCCGCCTTTC
TCCCTTCGGGAAGCGTGGCGCTTTCTCATAGCTCACGCTGTAGGTATCTCAGTT
CGGTGTAGGTCGTTCGCTCCAAGCTGGGCTGTGTGCACGAACCCCCCGTTCAG
CCCGACCGCTGCGCCTTATCCGGTAACTATCGTCTTGAGTCCAACCCGGTAAGA
CACGACTTATCGCCACTGGCAGCAGCCACTGGTAACAGGATTAGCAGAGCGAG
GTATGTAGGCGGTGCTACAGAGTTCTTGAAGTGGTGGCCTAACTACGGCTACAC
```

Figure 2 Cont.

TAGAAGGACAGTATTTGGTATCTGCGCTCTGCTGAAGCCAGTTACCTTCGGAAA
AAGAGTTGGTAGCTCTTGATCCGGCAAACAAACCACCGCTGGTAGCGGTGGTTT
TTTTGTTTGCAAGCAGCAGATTACGCGCAGAAAAAAGGATCTCAAGAAGATCC
TTTGATC

SEQUENCE LISTING

```
<160> NUMBER OF SEQ ID NOS: 2

<210> SEQ ID NO 1
<211> LENGTH: 630
<212> TYPE: PRT
<213> ORGANISM: Homo sapiens

<400> SEQUENCE: 1

Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
```

```
            195                 200                 205
Val Ser Cys Pro Gly Pro Leu Asp Gln Asp Gln Gln Glu Ala Ala Arg
210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
                260                 265                 270

Gln Arg Ser Ser Arg Asp Pro Ser Trp Arg Gln Pro Glu Arg Thr Ile
                275                 280                 285

Leu Arg Pro Arg Phe Arg Arg Glu Val Glu Lys Thr Ala Cys Pro Ser
290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
                340                 345                 350

Lys His Lys Leu Asp Glu Leu Tyr Pro Gln Gly Tyr Pro Glu Ser Val
                355                 360                 365

Ile Gln His Leu Gly Tyr Leu Phe Leu Lys Met Ser Pro Glu Asp Ile
                370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Ala Pro Arg Arg Pro Leu
                405                 410                 415

Pro Gln Val Ala Thr Leu Ile Asp Arg Phe Val Lys Gly Arg Gly Gln
                420                 425                 430

Leu Asp Lys Asp Thr Leu Asp Thr Leu Thr Ala Phe Tyr Pro Gly Tyr
                435                 440                 445

Leu Cys Ser Leu Ser Pro Glu Glu Leu Ser Ser Val Pro Pro Ser Ser
450                 455                 460

Ile Trp Ala Val Arg Pro Gln Asp Leu Asp Thr Cys Asp Pro Arg Gln
465                 470                 475                 480

Leu Asp Val Leu Tyr Pro Lys Ala Arg Leu Ala Phe Gln Asn Met Asn
                485                 490                 495

Gly Ser Glu Tyr Phe Val Lys Ile Gln Ser Phe Leu Gly Gly Ala Pro
                500                 505                 510

Thr Glu Asp Leu Lys Ala Leu Ser Gln Gln Asn Val Ser Met Asp Leu
                515                 520                 525

Ala Thr Phe Met Lys Leu Arg Thr Asp Ala Val Leu Pro Leu Thr Val
                530                 535                 540

Ala Glu Val Gln Lys Leu Leu Gly Pro His Val Glu Gly Leu Lys Ala
545                 550                 555                 560

Glu Glu Arg His Arg Pro Val Arg Asp Trp Ile Leu Arg Gln Arg Gln
                565                 570                 575

Asp Asp Leu Asp Thr Leu Gly Leu Gly Leu Gln Gly Gly Ile Pro Asn
                580                 585                 590

Gly Tyr Leu Val Leu Asp Leu Ser Met Gln Glu Ala Leu Ser Gly Thr
                595                 600                 605

Pro Cys Leu Leu Gly Pro Gly Pro Val Leu Thr Val Leu Ala Leu Leu
610                 615                 620
```

Leu Ala Ser Thr Leu Ala
625                 630

<210> SEQ ID NO 2
<211> LENGTH: 1893
<212> TYPE: DNA
<213> ORGANISM: Homo sapiens

<400> SEQUENCE: 2

| | | | | | |
|---|---|---|---|---|---|
| atggccttgc | caacggctcg | accoctgttg | gggtcctgtg | ggaccoccgc | cctcggcagc |    60 |
| ctcctgttcc | tgctcttcag | cctcggatgg | gtgcagccct | cgaggaccct | ggctggagag |   120 |
| acagggcagg | aggctgcgcc | cctggacgga | gtcctggcca | acccacctaa | catttccagc |   180 |
| ctctccoctc | gccaactcct | tggcttcccg | tgtgcggagg | tgtccggcct | gagcacggag |   240 |
| cgtgtccggg | agctggctgt | ggccttggca | cagaagaatg | tcaagctctc | aacagagcag |   300 |
| ctgcgctgtc | tggctcaccg | gctctctgag | cccccgagg | acctggacgc | cctcccattg |   360 |
| gacctgctgc | tattcctcaa | cccagatgcg | ttctcggggc | cccaggcctg | cacccgtttc |   420 |
| ttctcccgca | tcacgaaggc | caatgtggac | ctgctcccga | gggggctcc | cgagcgacag |   480 |
| cggctgctgc | ctgcggctct | ggcctgctgg | ggtgtgcggg | ggtctctgct | gagcgaggct |   540 |
| gatgtgcggg | ctctgggagg | cctggcttgc | gacctgcctg | ggcgctttgt | ggccgagtcg |   600 |
| gccgaagtgc | tgctacccog | gctggtgagc | tgcccgggac | ccctggacca | ggaccagcag |   660 |
| gaggcagcca | gggcggctct | gcagggcggg | gaccccocct | acggcccccc | gtcgacatgg |   720 |
| tctgtctcca | cgatggacgc | tctgcggggc | ctgctgcccg | tgctgggcca | gcccatcatc |   780 |
| cgcagcatcc | gcagggcat | cgtggccgcg | tggcggcaac | gctcctctcg | ggacccatcc |   840 |
| tggcggcagc | ctgaacggac | catcctccgg | ccgcggttcc | ggcgggaagt | ggagaagaca |   900 |
| gcctgtcctt | caggcaagaa | ggcccgcgag | atagacgaga | gcctcatctt | ctacaagaag |   960 |
| tgggagctgg | aagcctgcgt | ggatgcgcc | ctgctggcca | cccagatgga | ccgcgtgaac |  1020 |
| gccatcccct | tcacctacga | gcagctggac | gtcctaaagc | ataaactgga | tgagctctac |  1080 |
| ccacaaggtt | accccgagtc | tgtgatccag | cacctgggct | acctcttcct | caagatgagc |  1140 |
| cctgaggaca | ttcgcaagtg | gaatgtgacg | tccctggaga | ccctgaaggc | tttgcttgaa |  1200 |
| gtcaacaaag | ggcacgaaat | gagtcctcag | gctcctcggc | ggccoctccc | acaggtggcc |  1260 |
| accctgatcg | accgctttgt | gaagggaagg | ggccagctag | acaaagacac | cctagacacc |  1320 |
| ctgaccgcct | tctaccctgg | gtacctgtgc | tccctcagcc | ccgaggagct | gagctccgtg |  1380 |
| ccccccagca | gcatctgggc | ggtcaggccc | caggacctgg | acacgtgtga | cccaaggcag |  1440 |
| ctggacgtcc | tctatcccaa | ggcccgcctt | gctttccaga | acatgaacgg | gtccgaatac |  1500 |
| ttcgtgaaga | tccagtcctt | cctgggtggg | gccccacgg | aggatttgaa | ggcgctcagt |  1560 |
| cagcagaatg | tgagcatgga | cttggccacg | ttcatgaagc | tgcggacgga | tgcggtgctg |  1620 |
| ccgttgactg | tggctgaggt | gcagaaactt | ctggacccc | acgtggaggg | cctgaaggcg |  1680 |
| gaggagcggc | accgcccggt | gcgggactgg | atcctacggc | agcggcagga | cgacctggac |  1740 |
| acgtggggc | tggggctaca | gggcggcatc | cccaacggct | acctggtcct | agacctcagc |  1800 |
| atgcaagagg | ccctctcggg | gacgccctgc | ctcctaggac | ctggacctgt | tctcaccgtc |  1860 |
| ctggcactgc | tcctagcctc | caccctggcc | tga | | | 1893 |

MSLN TARGETING DNA VACCINE FOR CANCER IMMUNOTHERAPY

CROSS REFERENCE TO RELATED APPLICATIONS

This application is a continuation application of U.S. application Ser. No. 15/105,739, filed Jun. 17, 2016, which is a national stage application under 35 U.S.C. 371 and claims the benefit of PCT Application No. PCT/EP2014/003403 having an international filing date of 17 Dec. 2014, which designated the United States, which PCT application claimed the benefit of European Patent Application No. 13005896.9 filed 18 Dec. 2013, the disclosures of which are incorporated herein by reference in their entirety.

REFERENCE TO SEQUENCE LISTING

This application contains a Sequence Listing submitted as an electronic text file named "8263VAX-2_SequenceListing_2014049767.txt", having a size in bytes of 9000 bytes, and created on May 20, 2016. The information contained in this electronic file is hereby incorporated by reference in its entirety pursuant to 37 CFR § 1.52(e)(5).

FIELD OF THE INVENTION

The present invention relates to an attenuated mutant strain of Salmonella comprising a recombinant DNA molecule encoding Mesothelin. In particular, the present invention relates to the use of said attenuated mutant strain of Salmonella in cancer immunotherapy.

BACKGROUND OF THE INVENTION

Mesothelin is a glycosyl-phosphatidylinositol anchored glycoprotein present on the cell surface of various human solid tumors. Mesothelin was first identified with the monoclonal antibody (mAb)K1 (Chang et al., Cancer Research 52: 181-186, 1992). The Mesothelin (MSLN) gene encodes a 71-kDa precursor protein that is processed to a 40-kDa glycosyl-phosphatidylinositol anchored protein, the mature portion to which mAB K1 binds, termed Mesothelin, and a NH2-terminal 31-kDa fragment called megakaryocyte-potentiating factor that is released from the cell. Mesothelin is a tumor differentiation antigen present at low levels on a restricted set of normal adult tissues, such as mesothelium, but aberrantly overexpressed in mesotheliomas, ovarian and pancreatic cancers (Hassan et al., Clinical Cancer Research 10: 3937-3942, 2004). Thus, MSLN is a promising candidate for the development of cancer vaccines.

Mesothelin (MSLN) has been described as a target antigen for immunotherapy (Hassan et al., Clin Cancer Res, 10: 3937-3942, 2004). Several immunotherapeutic approaches have been used to target MSLN overexpressing tumor types. Hassan et al. (Clin Cancer Res, 10: 3937-39422004) discloses anti-mesothelin immunotoxin SS1P [SS1(dsFv) PE38] exhibiting antitumor activity in adult nude mice. In recent years, several early phase clinical trials based on the administration of anti-mesothelin immunotoxin SS1P or chimeric anti-mesothelin monoclonal antibody MORAb-009 via bolus injection or continuous intravenous infusion have been started (comprehensively summarized in Kelly et al., Mol Cancer Ther., 11(3):517-525, 2012). Another immunotherapeutic approach currently tested in phase VII clinical trials is based on the administration of anti-mesothelin modified lymphocytes (ClinicalTrials.gov; Identifyers NCT01355965 and NCT01439152). Dung et al. (Clin Cancer Res, 18(3):858-868, 2012) discloses a Listeria monocytogenes based mesothelin vaccine, which is administered intravenously. Yamasaki et al. (Int J Cancer, 133(1): 1-17, 2013) discloses and intravenous genetic Mesothelin vaccine based on human adenovirus 40.

Attenuated derivatives of Salmonella enterica are attractive vehicles for the delivery of heterologous antigens to the mammalian immune system, since S. enterica strains can potentially be delivered via mucosal routes of immunization, i.e. orally or nasally, which offers advantages of simplicity and safety compared to parenteral administration. Furthermore, Salmonella strains elicit strong humoral and cellular immune responses at the level of both systemic and mucosal compartments. Batch preparation costs are relatively low and formulations of live bacterial vaccines are highly stable. Attenuation can be accomplished by deletion of various genes, including virulence, regulatory, and metabolic genes.

Several Salmonella typhimurium strains attenuated by aro mutations have been shown to be safe and effective delivery vehicles for heterologous antigens in animal models.

Approaches of delivering DNA constructs encoding antigens, in particular the tumor stroma antigen VEGFR, via live attenuated Salmonella typhimurium strains into mouse target cells are described in WO 03/073995. Niethammer et al., (Nature Medicine 2002, 8(12), 1369) demonstrated that the attenuated S. typhimurium aroA strain SL7207 harboring an expression vector encoding the murine vascular endothelial growth factor receptor 2 (VEGFR-2 or FLK-1), which is essential for tumor angiogenesis, is functional as a cancer vaccine.

There is however only one attenuated Salmonella enterica serovar strain, namely Salmonella enterica serovar typhi Ty21a (short: S. typhi Ty21a), which has been accepted for use in humans and is distributed under the trade name of Vivotif® (Berna Biotech Ltd., a Crucell Company, Switzerland; marketing authorization number PL 15747/0001 dated 16 Dec. 1996).

This well-tolerated, live oral vaccine against typhoid fever was derived by chemical mutagenesis of the wild-type virulent bacterial isolate S. typhi Ty2 and harbors a loss-of-function mutation in the galE gene, as well as other less defined mutations. It has been licensed as typhoid vaccine in many countries after it was shown to be efficacious and safe in field trials.

WO 2013/091898 discloses a method for growing attenuated mutant Salmonella typhi strains lacking galactose epimerase activity and harboring a recombinant DNA molecule.

MSLN is a promising tumor antigen for the development of cancer vaccines. Major limitations of previously available MSLN vaccines are the administration via the intravenous route of administration and the associated side effects. The great need for improved cancer therapy approaches based on targeting MSLN has not been met so far.

OBJECTS OF THE INVENTION

In view of the prior art, it is an object of the present invention to provide a novel oral MSLN targeting cancer vaccine. Such a MSLN targeting cancer vaccine would offer major advantages for improving the treatment options for cancer patients.

SUMMARY OF THE INVENTION

In one aspect, the present invention relates to an attenuated mutant strain of Salmonella comprising at least one copy of a recombinant DNA molecule comprising an expression cassette encoding Mesothelin (MSLN).

The attenuated *Salmonella* strain of the present invention was shown to elicit a strong immune response in healthy mice. To the inventor's knowledge, this novel attenuated *Salmonella* strain is the first oral cancer vaccine targeting MSLN. Since MSLN is overexpressed in mesotheliomas, ovarian and pancreatic cancers, and a wide variety of other tumors, the attenuated *Salmonella* strain of the present invention has great potential as cancer vaccine for the treatment of these indications.

In a first study, the vaccine according to the present invention (VXM04) has been demonstrated to elicit a strong MSLN-specific immune response in healthy mice. These results indicate that vaccination with VXM04 may lead to an immune response and the development of an immune memory against tumor cells overexpressing MSLN. It is remarkable and surprising that the novel vaccine VXM04 is effective at relatively low doses. The attenuated *Salmonella* mutant strain of the present invention may be applied in monotherapy or in combination with a second attenuated mutant strain of *Salmonella* comprising a DNA molecule encoding a second tumor antigen. Furthermore, the attenuated mutant strain of the present invention may be administered in combination with chemotherapy, radiotherapy or biological cancer therapy. Treatment with VXM04 may also be effective, if the patient has developed a resistance to chemotherapy (chemo-refractory patients). The novel attenuated *Salmonella* strain of the present invention might therefore be useful in novel, greatly improved cancer therapy approaches.

In particular embodiments, the attenuated mutant strain of *Salmonella* is of the species *Salmonella enterica*. In particular embodiments, the attenuated mutant strain of *Salmonella* is *Salmonella typhi* Ty21a.

In particular embodiments, the expression cassette is a eukaryotic expression cassette.

In particular embodiments, MSLN is selected from the group consisting of human MSLN and a protein that shares at least about 80% sequence identity therewith.

In particular embodiments, the MSLN has the amino acid sequence as found in SEQ ID NO 1.

In particular embodiments, the recombinant DNA molecule comprises the kanamycin antibiotic resistance gene, the pMB1 ori, and a eukaryotic expression cassette encoding human MSLN or a protein that shares at least 80% sequence identity therewith under the control of a CMV promoter. In particular embodiments, human MSLN has the nucleic acid sequence as found in SEQ ID NO 2.

In particular embodiments, the attenuated mutant strain of *Salmonella* is for use as a medicament.

In particular embodiments, the attenuated mutant strain of *Salmonella* is for use as a vaccine.

In particular embodiments, the attenuated mutant strain of *Salmonella* is for use in cancer immunotherapy.

In particular embodiments, cancer immunotherapy further comprises administration of one or more further attenuated mutant strain(s) of *Salmonella* comprising at least one copy of a recombinant DNA molecule comprising an expression cassette encoding a tumor antigen and/or a tumor stroma antigen. In particular embodiments, said one or more further attenuated mutant strain(s) of *Salmonella* is/are *Salmonella typhi* Ty21a comprising a eukaryotic expression cassette. In particular embodiments, said one or more further strain(s) of *Salmonella* comprise(s) an attenuated mutant strain(s) of *Salmonella* encoding the tumor stroma antigen human VEGFR-2 and/or the tumor antigen human Wilms' Tumor Protein (WT1).

In particular embodiments, the attenuated mutant strain of *Salmonella* is co-administered with said one or more further attenuated mutant strain(s) of *Salmonella*.

In particular embodiments, cancer immunotherapy is accompanied by chemotherapy, radiotherapy or biological cancer therapy.

In particular embodiments, the attenuated mutant strain of *Salmonella* is administered during the chemotherapy or the radiotherapy treatment cycle or during biological cancer therapy.

In particular embodiments, the attenuated mutant strain of *Salmonella* is administered before the chemotherapy or the radiotherapy treatment cycle or before biological cancer therapy.

In particular embodiments, the attenuated mutant strain of *Salmonella* is administered after the chemotherapy or the radiotherapy treatment cycle or after biological cancer therapy.

In further embodiments the attenuated mutant strain of *Salmonella* is administered before and during at least one of the chemotherapy, the radiotherapy treatment cycle and the biological cancer therapy. In cases where more than one of the chemotherapy, the radiotherapy and the biological cancer therapy are carried out the attenuated mutant strain of *Salmonella* may be administered before or during or before and during at least one of these therapies, particularly during at least two of these therapies.

In particular embodiments, the attenuated mutant strain of *Salmonella* is administered orally.

In particular embodiments, the cancer is selected from mesotheliomas, ovarian and pancreatic cancers, squamous cell carcinomas of the cervix, head and neck, vulva, lung and esophagus, lung adenocarcinomas, endometrial carcinomas, biphasic synovial sarcomas, desmoplastic small round cell tumors and gastric adenocarcinomas.

In particular embodiments, the single dose is from about $10^5$ to about $10^{11}$, particularly from about $10^6$ to about $10^{10}$, more particularly from about $10^6$ to about $10^9$, more particularly from about $10^6$ to about $10^8$, most particularly from about $10^6$ to about $10^7$ colony forming units (CFU).

In particular embodiments, the attenuated mutant strain of *Salmonella* is for use in personalized cancer immunotherapy comprising the step of assessing the MSLN expression pattern and/or the pre-immune response against MSLN of a patient.

DETAILED DESCRIPTION OF THE INVENTION

The present invention may be understood more readily by reference to the following detailed description of the invention and the examples included therein.

In one aspect, the present invention relates to an attenuated mutant strain of *Salmonella* comprising at least one copy of a recombinant DNA molecule comprising an expression cassette encoding Mesothelin (MSLN).

According to the invention, the attenuated *Salmonella* strain functions as the bacterial carrier of the recombinant DNA molecule comprising an expression cassette encoding Mesothelin (MSLN) for the delivery of said recombinant DNA molecule into a target cell.

In the context of the present invention, the term "attenuated" refers to a bacterial strain of reduced virulence compared to the parental bacterial strain, not harboring the attenuating mutation. Attenuated bacterial strains have preferably lost their virulence but retained their ability to induce protective immunity. Attenuation can be accomplished by deletion of various genes, including virulence, regulatory, and metabolic genes. Attenuated bacteria may be found naturally or they may be produced artificially in the laboratory, for example by adaptation to a new medium or cell culture or they may be produced by recombinant DNA technology.

In the context of the present invention, the term "mutant strain" refers to a bacterial strain harboring a mutation in its genome. In this context, the term "mutation" refers to a change in a nucleic acid sequence, including point mutations, insertions, deletions, translocations and inversions.

In the context of the present invention, the term "comprises" or "comprising" means "including, but not limited to". The term is intended to be open-ended, to specify the presence of any stated features, elements, integers, steps or components, but not to preclude the presence or addition of one or more other features, elements, integers, steps, components or groups thereof. The term "comprising" thus includes the more restrictive terms "consisting of" and "essentially consisting of". In one embodiment the term "comprising" as used throughout the application and in particular within the claims may be replaced by the term "consisting of".

In the context of the present invention, the term "recombinant DNA molecule" refers to an engineered DNA construct, preferably composed of DNA pieces of different origin. The recombinant DNA molecule can be a linear nucleic acid, or preferably, a circular recombinant DNA plasmid generated by introducing an open reading frame encoding MSLN into an expression vector plasmid.

In the context of the present invention, the term "expression cassette" refers to a nucleic acid unit comprising at least the MSLN gene under the control of regulatory sequences controlling its expression. The expression cassette comprised in the attenuated mutant strain of *Salmonella* can preferably mediate transcription of the included open reading frame encoding MSLN in a target cell. Expression cassettes typically comprise a promoter, at least one open reading frame and a transcription termination signal.

Mesothelin is a 40-kDa cell surface glycoprotein present on normal mesothelial cells and overexpressed in several human tumors, including mesothelioma and ovarian and pancreatic adenocarcinoma. The Mesothelin gene encodes a precursor protein of 71-kDa that is processed to yield a 31-kDa shed protein named megakaryocyte-potentiating factor (MPF) and the 40-kDa cell bound fragment mesothelin. Mesothelin was shown to exhibit megakaryocyte-colony-forming activity in the presence of interleukin-3. Mesothelin is a tumor differentiation antigen present at low levels on a restricted set of normal adult tissues, such as mesothelium, but aberrantly overexpressed in a wide variety of human tumors including mesotheliomas, ovarian and pancreatic cancers, squamous cell carcinomas of the cervix, head and neck, vulva, lung and esophagus, lung adenocarcinomas, endometrial carcinomas, biphasic synovial sarcomas, desmoplastic small round cell tumors and gastric adenocarcinomas. The normal biological function of Mesothelin is unknown. Studies in mesothelin knock-out mice revealed no detectable phenotype, and both male and female mice produced healthy off-spring. Studies in pancreatic cancer suggest that Mesothelin plays a role in tumorigenesis by increasing cellular proliferation, migration, and S-phase cell populations. Furthermore, there is evidence that Mesothelin is an immunogenic protein. Due to its expression profile, its oncogenic functions and its immunogenic potential, the tumor antigen mesothelin is a promising candidate for the development of cancer vaccines.

Mesothelin is a tumor differentiation antigen present at low levels on a restricted set of normal adult tissues, such as mesothelium, but aberrantly overexpressed in mesotheliomas, ovarian and pancreatic cancers (Hassan et al., *Clin Cancer Res*, 10: 3937-3942, 2004). Thus, MSLN is a promising candidate for the development of cancer vaccines.

In particular embodiments, the attenuated mutant strain of *Salmonella* is of the species *Salmonella enterica*. In particular embodiments, the attenuated mutant strain of *Salmonella* is *Salmonella typhi* Ty21a. The attenuated *S. typhi* Ty21a strain is the active component of Typhoral L®, also known as Vivotif® (manufactured by Berna Biotech Ltd., a Crucell Company, Switzerland). It is currently the only licensed live oral vaccine against typhoid fever. This vaccine has been extensively tested and has proved to be safe regarding patient toxicity as well as transmission to third parties (Wandan et al., J. Infectious Diseases 1982, 145:292-295). The vaccine is licensed in more than 40 countries. The Marketing Authorization number of Typhoral L® is PL 15747/0001 dated 16 Dec. 1996. One dose of vaccine contains at least $2 \times 10^9$ viable *S. typhi* Ty21a colony forming units and at least $5 \times 10^9$ non-viable *S. typhi* Ty21a cells.

One of the biochemical properties of the *Salmonella typhi* Ty21a bacterial strain is its inability to metabolize galactose. The attenuated bacterial strain is also not able to reduce sulfate to sulfide which differentiates it from the wild-type *Salmonella typhi* Ty2 strain. With regard to its serological characteristics, the *Salmonella typhi* Ty21a strain contains the O9-antigen which is a polysaccharide of the outer membrane of the bacteria and lacks the O5-antigen which is in turn a characteristic component of *Salmonella typhimurium*. This serological characteristic supports the rationale for including the respective test in a panel of identity tests for batch release.

In particular embodiments, the expression cassette is a eukaryotic expression cassette. In the context of the present invention, the term "eukaryotic expression cassette" refers to an expression cassette which allows for expression of the open reading frame in a eukaryotic cell. It has been shown that the amount of heterologous antigen required to induce an adequate immune response may be toxic for the bacterium and result in cell death, over-attenuation or loss of expression of the heterologous antigen. Using a eukaryotic expression cassette that is not expressed in the bacterial vector but only in the target cell may overcome this toxicity problem and the protein expressed may exhibit a eukaryotic glycosylation pattern.

A eukaryotic expression cassette comprises regulatory sequences that are able to control the expression of an open reading frame in a eukaryotic cell, preferably a promoter and a polyadenylation signal. Promoters and polyadenylation signals included in the recombinant DNA molecules comprised by the attenuated mutant strain of *Salmonella* of the present invention are preferably selected to be functional within the cells of the subject to be immunized. Examples of suitable promoters, especially for the production of a DNA vaccine for humans, include but are not limited to promoters from Cytomegalovirus (CMV), such as the strong CMV immediate early promoter, Simian Virus 40 (SV40), Mouse Mammary Tumor Virus (MMTV), Human Immunodeficiency Virus (HIV), such as the HIV Long Terminal Repeat (LTR) promoter, Moloney virus, Epstein Barr Virus (EBV), and from Rous Sarcoma Virus (RSV) as well as promoters from human genes such as human actin, human myosin, human hemoglobin, human muscle creatine, and human metallothionein. In a particular embodiment, the eukaryotic expression cassette contains the CMV promoter. In the context of the present invention, the term "CMV promoter" refers to the strong immediate-early cytomegalovirus promoter.

Examples of suitable polyadenylation signals, especially for the production of a DNA vaccine for humans, include but are not limited to the bovine growth hormone (BGH) polyadenylation site, SV40 polyadenylation signals and LTR polyadenylation signals. In a particular embodiment, the eukaryotic expression cassette included in the recombinant DNA molecule comprised by the attenuated mutant strain of *Salmonella* of the present invention comprises the BGH polyadenylation site.

In addition to the regulatory elements required for expression of the heterologous MSLN gene, like a promoter and a polyadenylation signal, other elements can also be included in the recombinant DNA molecule. Such additional elements include enhancers. The enhancer can be, for example, the enhancer of human actin, human myosin, human hemoglobin, human muscle creatine and viral enhancers such as those from CMV, RSV and EBV.

Regulatory sequences and codons are generally species dependent, so in order to maximize protein production, the regulatory sequences and codons are preferably selected to be effective in the species to be immunized. The person skilled in the art can produce recombinant DNA molecules that are functional in a given subject species.

In particular embodiments, MSLN is selected from the group consisting of human MSLN and a protein that shares at least about 80% sequence identity therewith.

In this context, the term "about" or "approximately" means within 80% to 120%, alternatively within 90% to 110%, including within 95% to 105% of a given value or range.

In the context of the present invention, the term "protein that shares at least about 80% sequence identity with human MSLN" refers to a protein that differs in the amino acid sequence and/or the nucleic acid sequence encoding the amino acid sequence of human MSLN. The protein may be of natural origin, e.g. a homolog of MSLN of a different species, or an engineered protein, e.g. an engineered MSLN derivative. It is known that the usage of codons is different between species. Thus, when expressing a heterologous protein in a target cell, it may be necessary, or at least helpful, to adapt the nucleic acid sequence to the codon usage of the target cell. Methods for designing and constructing derivatives of a given protein are well known to anyone of ordinary skill in the art.

The protein that shares at least about 80% sequence identity with human MSLN may contain one or more mutations comprising an addition, a deletion and/or a substitution of one or more amino acids. According to the teaching of the present invention, said deleted, added and/or substituted amino acids may be consecutive amino acids or may be interspersed over the length of the amino acid sequence of the protein that shares at least about 80% sequence identity with human MSLN. According to the teaching of the present invention, any number of amino acids may be added, deleted, and/or substitutes, as long as the sequence identity with human MSLN is at least about 80%. In particular embodiments, the sequence identity with human MSLN is at least about 80%, at least about 85%, at least about 90%, or most particularly at least about 95%. Methods and algorithms for determining sequence identity including the comparison of a parental protein and its derivative having deletions, additions and/or substitutions relative to a parental sequence, are well known to the practitioner of ordinary skill in the art. On the DNA level, the nucleic acid sequences encoding the protein that shares at least about 80% sequence identity with human MSLN may differ to a larger extent due to the degeneracy of the genetic code.

In particular embodiments, MSLN has the amino acid sequence as found in SEQ ID NO 1.

In particular embodiments, the recombinant DNA molecule comprises the kanamycin antibiotic resistance gene, the pMB1 ori, and a eukaryotic expression cassette encoding human MSLN or a protein that shares at least 80% sequence identity therewith under the control of a CMV promoter. In particular embodiments, human MSLN has the nucleic acid sequence as found in SEQ ID NO 2.

In particular embodiments, the recombinant DNA molecule is derived from commercially available pVAX1™ expression plasmid (Invitrogen, San Diego, Calif.). This expression vector was modified by replacing the high copy pUC origin of replication by the low copy pMB1 origin of replication of pBR322. The low copy modification was made in order to reduce the metabolic burden and to render the construct more stable. The generated expression vector backbone was designated pVAX10. Inserting human MSLN with the nucleic acid sequence as found in SEQ ID NO 2 into this expression vector backbone via NheI/XhoI yielded the expression plasmid pVAX10.hMSLN. The expression plasmid pVAX10.hMSLN is schematically depicted in FIG. 3.

In particular embodiments, the attenuated mutant strain of *Salmonella* is for use as a medicament.

In particular embodiments, the attenuated mutant strain of *Salmonella* is for use as a vaccine.

In the context of the present invention, the term "vaccine" refers to an agent which is able to induce an immune response in a subject upon administration. A vaccine can preferably prevent, ameliorate or treat a disease. A vaccine in accordance with the present invention comprises an attenuated mutant strain of *Salmonella*, preferably *S. typhi* Ty21a. The vaccine in accordance with the present invention further comprises at least one copy of a recombinant DNA molecule comprising an expression cassette, preferably a eukaryotic expression cassette, encoding MSLN, preferably selected from human MSLN or a protein that shares at least about 80% sequence identity therewith.

The live attenuated *Salmonella* mutant strain according to the present invention comprising a recombinant DNA molecule encoding MSLN can be used as a vehicle for the oral delivery of this recombinant DNA molecule. Such a delivery vector comprising a DNA molecule encoding a heterologous antigen, such as MSLN, is termed DNA vaccine.

Genetic immunization might be advantageous over conventional vaccination. The target DNA can be detected for a considerable period of time thus acting as a depot of the antigen. Sequence motifs in some plasmids, like GpC islands, are immunostimulatory and can function as adjuvants furthered by the immunostimulation due to LPS and other bacterial components.

Live bacterial vectors produce their own immunomodulatory factors such as lipopolysaccharides (LPS) in situ which may constitute an advantage over other forms of administration such as microencapsulation. Moreover, the use of the natural route of entry proves to be of benefit since many bacteria, like *Salmonella*, egress from the gut lumen via the M cells of Peyer's patches and migrate eventually into the lymph nodes and spleen, thus allowing targeting of vaccines to inductive sites of the immune system. The vaccine strain of *Salmonella typhi*, Ty21a, has been demonstrated to-date to have an excellent safety profile. Upon exit from the gut lumen via the M cells, the bacteria are taken up by phagocytic cells, such as macrophages and dendritic cells. These cells are activated by the pathogen and start to differentiate, and probably migrate into the lymph nodes and spleen. Due to their attenuating mutations, bacteria of the *S. typhi* Ty21 strain are not able to persist in these phagocytic cells but die at this time point. The recombinant DNA molecules are released and subsequently transferred into the cytosol of the phagocytic immune cells, either via a specific transport system or by endosomal leakage. Finally, the recombinant DNA molecules enter the nucleus, where they are transcribed, leading to MSLN expression in the cytosol of the phagocytic cells. Specific cytotoxic T cells against MSLN are induced by the activated antigen presenting cells.

There is no data available to-date indicating that *S. typhi* Ty21a is able to enter the bloodstream systemically. The live attenuated *Salmonella typhi* Ty21a vaccine strain thus allows specific targeting of the immune system while exhibiting an excellent safety profile. In contrast, adenovirus-based DNA vaccines might bear an inherent risk of unintended virus replication.

Attenuated derivatives of *Salmonella enterica* are attractive as vehicles for the delivery of heterologous antigens to the mammalian immune system because *S. enterica* strains can potentially be delivered via mucosal routes of immunization, i.e. orally or nasally, which offers advantages of simplicity and safety compared to parenteral administration. Furthermore, *Salmonella* strains elicit strong humoral and cellular immune responses at the level of both systemic and mucosal compartments.

In particular embodiments, the attenuated mutant strain of *Salmonella* is for use in cancer immunotherapy.

In particular embodiments, cancer immunotherapy further comprises administration of one or more further attenuated mutant strain(s) of *Salmonella* comprising at least one copy of a recombinant DNA molecule comprising an expression cassette encoding a tumor antigen and/or a tumor stroma antigen. In particular embodiments, said one or more further mutant strain(s) of *Salmonella* is/are *Salmonella typhi* Ty21a comprising a eukaryotic expression cassette. In particular embodiments, said one or more further strain(s) of *Salmonella* comprise(s) an attenuated mutant strain of *Salmonella* encoding human VEGFR-2 and/or human Wilms' Tumor Protein (WT1).

Combining the attenuated mutant strain of *Salmonella* of the present invention with a second attenuated mutant strain comprising a DNA molecule encoding a second tumor antigen may have synergistic antitumor effects. In particular, simultaneous targeting of different tumor antigens may minimize the risk of tumor escape. Combining MSLN based cancer immunotherapy with VEGFR-2 based immunotherapy may prove especially effective, since MSLN overexpressing tumor cells and the tumor vasculature are attacked at the same time.

In particular embodiments, the attenuated mutant strain of *Salmonella* is co-administered with said one or more further attenuated mutant strain(s) of *Salmonella*.

In the context of the present invention, the term "co-administration" or "co-administer" means administration of two different attenuated mutant strains of *Salmonella* within three consecutive days, more particularly within two consecutive days, more particularly on the same day, more particularly within 12 hours. Most particularly, in the context of the present invention, the term "co-administration" refers to simultaneous administration of two different attenuated mutant strains of *Salmonella*.

In particular embodiments, cancer immunotherapy is accompanied by chemotherapy, radiotherapy or biological cancer therapy. For cure of cancer, complete eradication of cancer stem cells may be essential. For maximal efficacy, a combination of different therapy approaches may be beneficial.

In the context of the present invention, the term "biological cancer therapy" refers to cancer therapy involving the use of living organisms, substances derived from living organisms, or laboratory-produced versions of such substances. Some biological therapies for cancer aim at stimulating the body's immune system to act against cancer cells (so called biological cancer immunotherapy). Biological cancer therapy approaches include the delivery of tumor antigens, delivery of therapeutic antibodies as drugs, administration of immunostimulatory cytokines and administration of immune cells. Therapeutic antibodies include antibodies targeting tumor antigens or tumor stroma antigens as well as antibodies functioning as checkpoint inhibitors, such as anti-PD-1, anti-PD-L1 and anti-CTLA4.

Chemotherapeutic agents that may be used in combination with the attenuated mutant strain of *Salmonella* of the present invention may be, for example: gemcitabine, amifostine (ethyol), cabazitaxel, cisplatin, dacarbazine (DTIC), dactinomycin, docetaxel, mechlorethamine, streptozocin, cyclophosphamide, carmustine (BCNU), lomustine (CCNU), doxorubicin (adriamycin), doxorubicin lipo (doxil), folinic acid, gemcitabine (gemzar), daunorubicin, daunorubicin lipo (daunoxome), procarbazine, ketokonazole, mitomycin, cytarabine, etoposide, methotrexate, 5-fluorouracil (5-FU), vinblastine, vincristine, bleomycin, paclitaxel (taxol), docetaxel (taxotere), aldesleukin, asparaginase, busulfan, carboplatin, cladribine, cam ptothecin, CPT-11, 10-hydroxy-7-ethyl-camptothecin (SN38), dacarbazine, floxuridine, fludarabine, hydroxyurea, ifosfamide, idarubicin, mesna, interferon alpha, interferon beta, irinotecan, mitoxantrone, topotecan, leuprolide, megestrol, melphalan, mercaptopurine, oxaliplatin, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil and combinations thereof.

Most preferred chemotherapeutic agents according to the invention in combination with VXM04 are cabazitaxel, carboplatin, oxaliplatin, cisplatin, cyclophosphamide, docetaxel, gemcitabine, doxorubicin, paclitaxel (taxol), irinotecan, vincristine, vinblastine, vinorelbin, folinic acid, 5-fluorouracil and bleomycin, especially gemcitabine.

It may be also favorable dependent on the occurrence of possible side effects, to include treatment with antibiotics or anti-inflammatory agents.

Should adverse events occur that resemble hypersensitivity reactions mediated by histamine, leukotrienes, or cytokines, treatment options for fever, anaphylaxis, blood pressure instability, bronchospasm, and dyspnoea are available. Treatment options in case of unwanted T-cell derived auto-aggression are derived from standard treatment schemes in acute and chronic graft vs. host disease applied after stem cell transplantation. Cyclosporin and glucocorticoids are proposed as treatment options.

In the unlikely case of systemic *Salmonella typhi* Ty21a type infection, appropriate antibiotic therapy is recommended, for example with fluoroquinolones including ciprofloxacin or ofloxacin. Bacterial infections of the gastrointestinal tract are to be treated with respective agents, such as rifaximin.

In particular embodiments, the attenuated mutant strain of *Salmonella* is administered during the chemotherapy or the radiotherapy treatment cycle or during biological cancer therapy.

In particular embodiments, the attenuated mutant strain of *Salmonella* is administered before the chemotherapy or the radiotherapy treatment cycle or before biological cancer therapy. This approach may have the advantage that chemotherapy or radiotherapy can be performed under conditions of enhanced cancer immunity.

In particular embodiments, the attenuated mutant strain of *Salmonella* is administered after the chemotherapy or the radiotherapy treatment cycle or after biological cancer therapy.

In particular embodiments, the attenuated mutant strain of *Salmonella* is administered orally. Oral administration is simpler, safer and more comfortable than parenteral administration. In contrast, intravenous administration of live bacterial vaccines such as the *Listeria monocytogenes* based mesothelin vaccine described in Dung et al., (Clin Cancer Res, 18(3):858-8682012) initially causes a bacteremia associated with safety risks of the sepsis-type. Thus, intravenous administration of live bacterial vaccines calls for careful observation and monitoring of clinical symptoms such as cytokine release. Oral administration of the attenuated mutant strain of the present invention may at least in part overcome the described risks. However, it has to be noted that the attenuated mutant strain of *Salmonella* of the present invention may also be administered by any other suitable route. Preferably, a therapeutically effective dose is administered to the subject, and this dose depends on the particular application, the type of malignancy, the subject's weight, age, sex and state of health, the manner of administration and the formulation, etc. Administration may be single or multiple, as required.

The attenuated mutant strain of *Salmonella* of the present invention may be provided in the form of a solution, a suspension, lyophilisate, or any other suitable form. It may be provided in combination with pharmaceutically acceptable carriers, diluents, and/or excipients. Agents for adjusting the pH value, buffers, agents for adjusting toxicity, and the like may also be included. In the context of the present invention, the term "pharmaceutically acceptable" refers to molecular entities and other ingredients of pharmaceutical compositions that are physiologically tolerable and do not typically produce untoward reactions when administered to a mammal (e.g., human). The term "pharmaceutically acceptable" may also mean approved by a regulatory agency of a Federal or a state government or listed in the U.S. Pharmacopeia or other generally recognized pharmacopeia for use in mammals, and, more particularly, in humans.

In particular embodiments, the cancer is selected from mesotheliomas, ovarian and pancreatic cancers, squamous cell carcinomas of the cervix, head and neck, vulva, lung and esophagus, lung adenocarcinomas, endometrial carcinomas, biphasic synovial sarcomas, desmoplastic small round cell tumors and gastric adenocarcinomas.

The vaccine of the present invention is surprisingly effective at relatively low doses. In particular embodiments, the single dose is from about $10^5$ to about $10^{11}$, particularly from about $10^6$ to about $10^{10}$, more particularly from about $10^6$ to about $10^9$, more particularly from about $10^6$ to about $10^8$, most particularly from about $10^6$ to about $10^7$ colony forming units (CFU). Administration of low doses of this live bacterial vaccine minimizes the risk of excretion and thus of transmission to third parties.

In this context, the term "about" or "approximately" means within a factor of 3, alternatively within a factor of 2, including within a factor of 1.5 of a given value or range.

In particular embodiments, the attenuated mutant strain of *Salmonella* is for use in individualized cancer immunotherapy comprising the step of assessing the MSLN expression pattern and/or the pre-immune response against MSLN of a patient.

VXM04 can be used—either by itself or in combination with other *Salmonella typhi* Ty21a based cancer vaccines comprising eukaryotic expression systems—for the treatment of various cancer types. In particular embodiments, VXM04 may be used for individualized patient specific cancer treatment. For that purpose, the patient's tumor and/or stromal antigen expression pattern and/or the patient's pre-immune responses against tumor and/or stromal antigens may be assessed in a first step for example by companion diagnostics targeting the patient's specific tumor and/or stromal antigen pattern. Depending on the patient's tumor and/or stromal antigen expression pattern or the patient's pre-immune responses against tumor and/or stromal antigens, VMX04 may be administered either alone or in combination with one or more suitable further *Salmonella typhi* Ty21a based cancer vaccine(s) comprising eukaryotic expression systems. Combinations of VXM04 with one or more further *Salmonella typhi* Ty21a based cancer vaccine(s) may however also be administered as fixed combinations. These cocktails combining two or more *Salmonella typhi* Ty21a based cancer vaccines can be composed from separate off the shelf products. The combinations, either fixed or individualized may contain VXM01 (WO 2013/091898) as anti-angiogenic basis therapy.

SHORT DESCRIPTION OF FIGURES AND TABLES

FIG. 1: Amino acid sequence (SEQ ID NO:1) of human MSLN encoded by MSLN cDNA contained in plasmid pVAX10.hMSLN FIG. 2: Nucleic acid sequence (SEQ ID NO:2) of pVAX10.hMSLN FIG. 3: Plasmid map of pVAX10.hMSLN FIG. 4: Percentages of Meso-specific CD8+ cells in spleens from healthy C57Bl/6 mice as detected by MSLN-GSL-Penta. Individual percentages of the entirety of mice treated with VXM-04m-empty in comparison to the entirety of mice treated with VXM-04m are shown.

Figure 5:
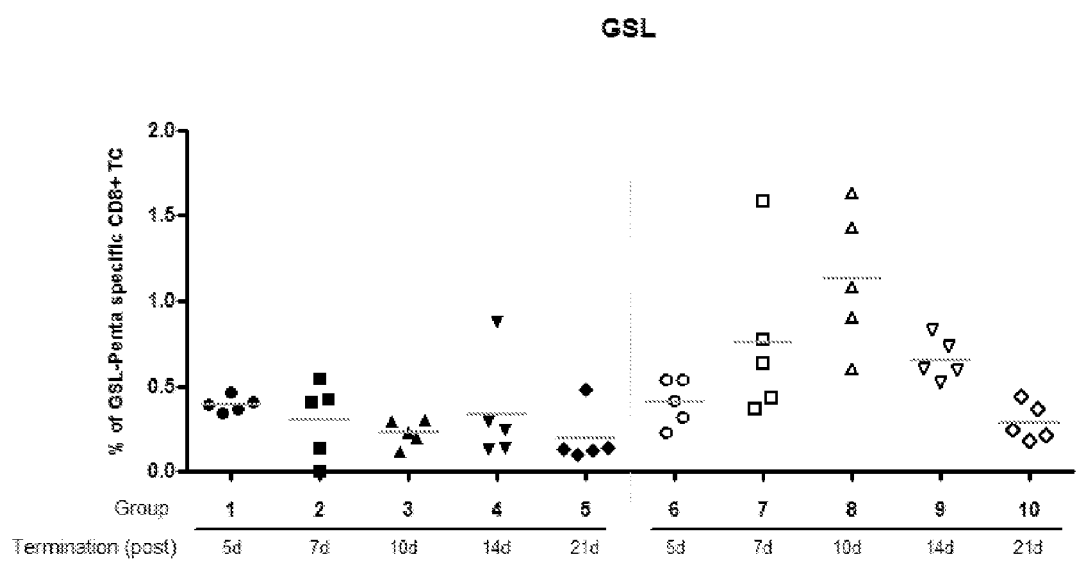

FIG. 5: Percentages of Meso-specific CD8+ cells in spleens from healthy C57Bl/6 mice as detected by MSLN-GSL-Penta. Individual percentages partitioned according to the treatment groups are shown.

Figure 6:
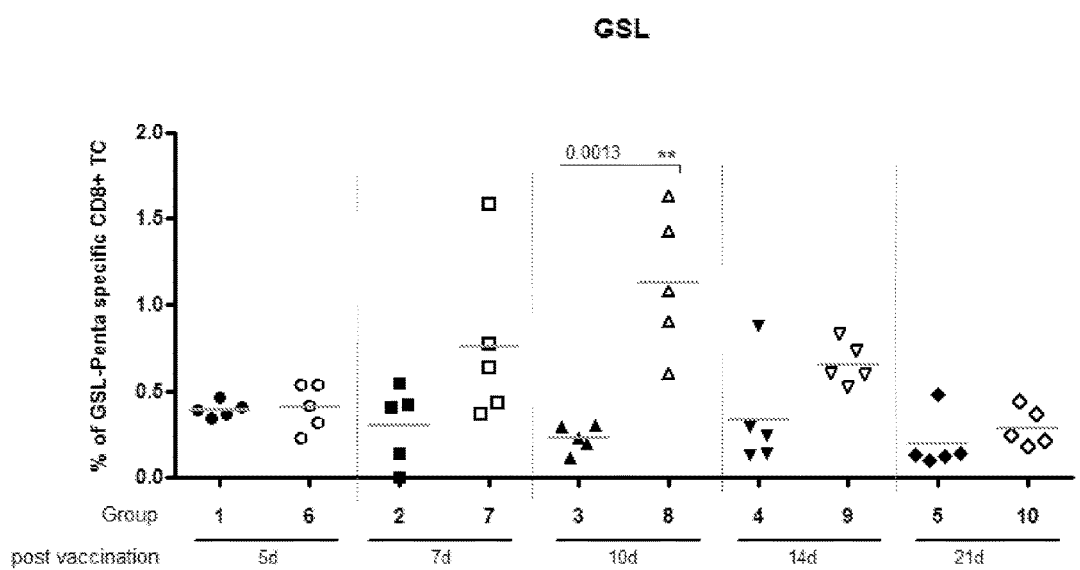

FIG. 6: Percentages of Meso-specific CD8+ cells in spleens from healthy C57Bl/6 mice as detected by MSLN-GSL-Penta. Individual percentages partitioned according to the treatment groups are shown.

Figure 7:
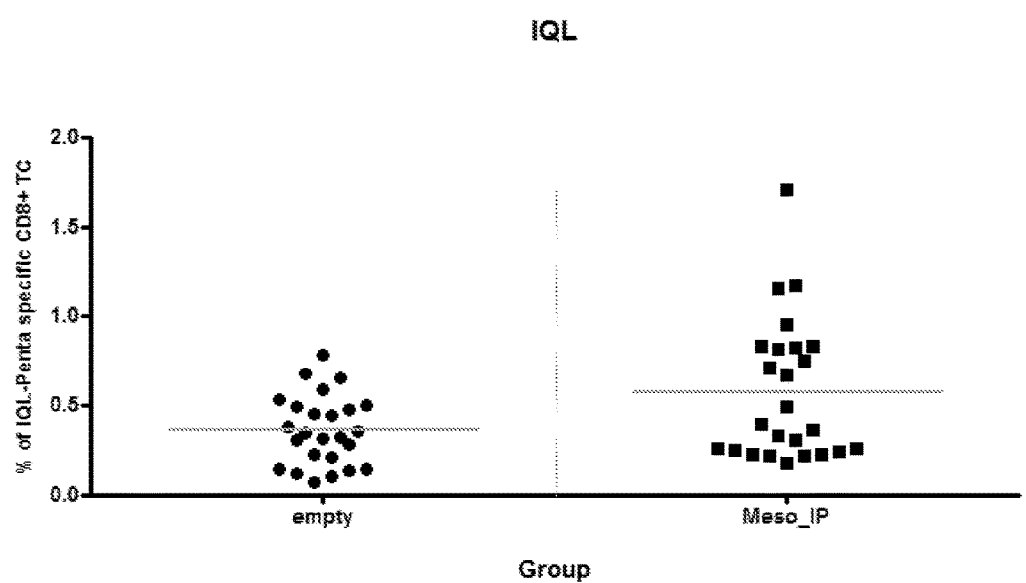

FIG. 7: Percentages of Meso-specific CD8+ cells in spleens from healthy C57Bl/6 mice as detected by MSLN-IQL-Penta. Individual percentages of the entirety of mice treated with VXM-04m-empty in comparison to the entirety of mice treated with VXM-04m are shown.

Figure 8:
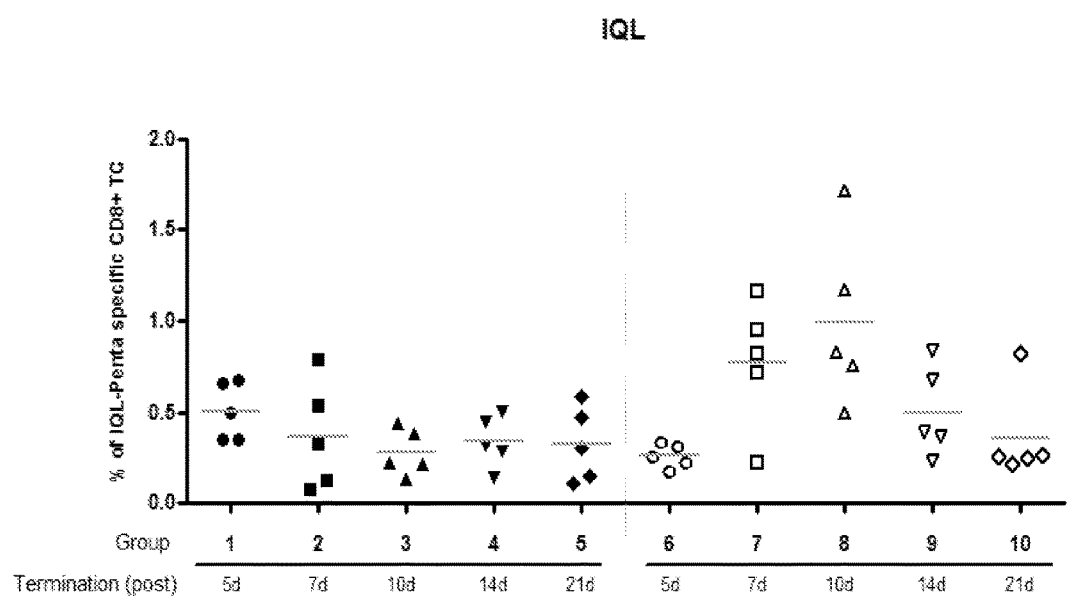

FIG. 8: Percentages of Meso-specific CD8+ cells in spleens from healthy C57Bl/6 mice as detected by MSLN-IQL-Penta. Individual percentages partitioned according to the treatment groups are shown.

Figure 9:
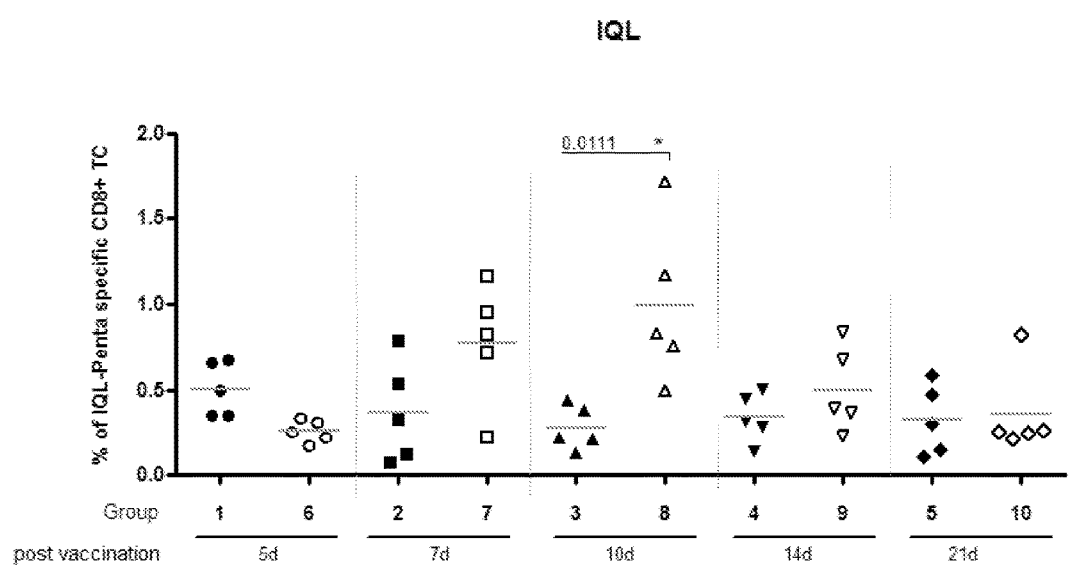

FIG. 9: Percentages of Meso-specific CD8+ cells in spleens from healthy C57Bl/6 mice as detected by MSLN-IQL-Penta. Individual percentages partitioned according to the treatment groups are shown.

Table 1: Pro5® Recombinant MHC Pentamers used in the Pentamer analysis.

EXAMPLES

Example 1: Preparation of Recombinant Plasmids pVAX10.mMSLN and pVAX10.hMSLN Human MSLN (1893 bp, MSLN sequence according to NCBI reference sequence NM_013404.4) and murine MSLN (1878 bp, MSLN sequence according to NCBI reference sequence NM_018857.1) were cloned into the pVAX10 backbone derived of pVAX10.VR2-1. MSLN DNA fragments were generated by double-strand gene synthesis, where oligonucleotides were linked together using a thermostable ligase. The obtained ligation products were amplified by PCR. Upon amplification, the in vitro synthesized DNA fragments of human and murine MSLN were cloned into the pVAX10 backbone via NheI/XhoI (the VEGFR-2 coding region of recombinant plasmid pVAX10.VR2-1 was replaced by human or murine MSLN). For quality control, the entire plasmids were sequenced and aligned to the respective reference sequence after transformation into *E. coli*. Both sequences proved to be free of errors. The resulting plasmids were designated pVAX10.mMSLN and pVAX10.hMSLN.

Example 2: Transformation of Attenuated Salmonella Strains with the Recombinant Plasmids

*S. typhi* Ty 21a was transformed with plasmid pVAX10.hMSLN. *S. typhimurium* SL7207 (aroA$^-$) was transformed with plasmid pVAX10.mMSLN. The transformation was performed by electroporation.

Preparation of Competent *Salmonella* Cells:

Glycerol cultures of *S. typhi* Ty21a and *S. typhimurium* SL7207 were inoculated on LB plates (animal component free [ACF] soy peptone). The plates were incubated at 37° C. overnight. One colony each was used for overnight-liquid-preculture. 3 ml LB medium (ACF soy peptone) inoculated with one colony each was incubated at 37° C. and 180 rpm overnight. To prepare competent cells, 2×300 ml of LB medium (ACF soy peptone) were inoculated with 3 ml of the overnight culture and incubated at 37° C. and 180 rpm up to an $OD_{600}$ of about 0.5. The cultures were then put on ice for 10 minutes. Subsequently, the bacteria were centrifuged for 10 minutes at 3000×g at 4° C. and each pellet was resuspended in 500 mL of ice cold $H_2O_{dest}$. After a new centrifugation step, the bacterial pellets were washed twice in 10% ice cold glycerol. Both pallets were put together in 2 ml of 10% glycerol and finally frozen in aliquots of 50 µL on dry ice. The used glycerol did not contain any animal ingredients (Sigma Aldrich, G5150).

Transformation of Competent *Salmonella* Cells:

For each transformation reaction, a 50 µl aliquot of competent cells was thawed on ice for 10 minutes. After adding 3-5 µL of plasmid DNA (pVAX10.hMSLN for competent *S. typhi* Ty21a cells and pVAX10.mMSLN for competent *S. typhimurium* SL7207 cells) the mixtures were incubated on ice for five minutes. Subsequently, the mixtures were transferred to pre-cooled cuvettes (1 mm thickness). The electric pulse was carried out at 12.5 kV/cm. Immediately afterwards, 1 ml of LB medium (ACF soy peptone) was added to the cells, the cells were transferred into a 2 ml Eppendorf tube and shaken for 1 hour at 37° C. After a short centrifugation step on a bench centrifuge (16600 rcf, 20 s), the bacterial pellet was resuspended in 200 µl of LB (ACF soy peptone) antibiotic-free medium. The mixtures were applied with a Drigalski spatula on LB plates (ACF soy peptone) containing kanamycin (concentration=25 µg/ml or 50 µg/ml). The plates were incubated at 37° C. overnight.

Plasmid Preparation of Recombinant *Salmonella* Clones:

Three clones of each recombinant *Salmonella* strain were incubated overnight in 3 ml of LB medium (ACF soy peptone) containing kanamycin (50 µg/ml) at 37° C. The bacterial culture was then pelleted by centrifugation (16600 rcf, 30 s). Plasmid isolation was performed using the NucleoSpin Plasmid Kit from Macherey-Nagel. The plasmid DNA was eluted from the silica gel columns with 50 µl water. 5 µl of the eluate was used in agarose gel electrophoresis for control.

For long-term storage, 1 ml glycerol cultures of the positive clones were produced. For this purpose, 172 µl glycerol (no animal ingredients) was added to 828 µl medium of a logarithmically growing 3 ml culture in a 1 low ml screw microtube. The samples were stored at −70° C. until further use.

Complete Sequencing of Recombinant Plasmid DNA Isolated from *Salmonella*:

3 ml of liquid LB-Kan medium (ACF soy peptone) were inoculated with one colony of recombinant *Salmonella* (*S. typhi* Ty21a harboring pVAX10.hMSLN and *S. typhimurium* SL7207 harboring pVAX10.mMSLN) and incubated overnight at 37° C. and 180 rpm. The overnight culture was pelleted by centrifugation at 1300 rpm for 30 s on a bench centrifuge (Biofuge pico, Heraeus). The plasmid isolation was performed with the NucleoSpin Plasmid Kit from Macherey-Nagel. After alkaline lysis and precipitation of high molecular weight genomic DNA and cellular components, the plasmid DNA was loaded onto columns with a silica membrane. After a washing step, the plasmids were eluted from the column with 50 µl of sterile water and sequenced. The sequences were then compared with the respective reference sequence by clone specific alignments, i.e. the plasmid sequences of each *Salmonella* clone was one by one aligned with the reference sequence. All sequences were in line with the respective reference sequences. The recombinant *Salmonella* strains were designated VXM04 (*S. typhi* Ty21a harboring plasmid pVAX10.hMSLN) and VXM04m (*S. typhimurium* SL7207 harboring plasmid pVAX10.mMSLN).

Example 3: Assessing Immunekinetics of VXM04m in Healthy C57Bl/6 Mice

The kinetics of specific immune activation against murine Mesothelin in healthy C57Bl/6 mice was evaluated by Pentamer analysis and ELISpot. As negative control, a vector control group (receiving VXM04m-empty=*Salmonella typhimurium* containing no expression plasmid) was included in the study setup to discriminate the desired immunologic effect from any unspecific background stimulation caused by *Salmonella* empty vector. Immune monitoring was carried out at D5, D7, D10, D14 and D21 post vaccination after 4-fold every second day vaccination with VXM04m and VXM04m-empty (each $10^{10}$ CFU/dose).

1. Animal Maintenance 52 healthy female C57Bl/6 mice, 6 weeks old at reception, were obtained from JANVIER (Le Genest St Isle, France) and observed for 7 days in a specific-pathogen-free (SPF) animal care unit before starting the procedure. Animals were maintained in rooms under controlled conditions of temperature (23±2° C.), humidity (45±10%), photoperiod (12 h light/12 h dark) and air exchange. Animals were maintained in SPF conditions. Room temperature and humidity were continuously monitored. The air handling system was programmed for 14 air changes/hour, with no recirculation. Fresh outside air was passed through a series of filters, before being diffused evenly into each room. A positive pressure (20±4 Pa) was maintained in the experimentation room to prevent contamination or the spread of pathogens within a rodent colony. Animals were housed in polycarbonate cages (Techniplast, Limonest, France) that were equipped to provide food and water. The standard area cages used were 800 $cm^2$ with a maximum of 10 mice per cage (from the same group). Bedding for animals was sterile corn cob bedding (ref: LAB COB 12, SERLAB, Cergy-Pontoise, France), replaced twice a week. Animal wood was purchased from DIETEX (Saint-Gratien, France). Irradiated RM1 was used as sterile controlled granules. Food was provided ad libitum from water bottles equipped with rubber stoppers and snipper tubes. Water bottles were sterilized by sterile filtration and replaced twice a week. At D0, 50 mice out of 52 were distributed according to their individual body weight into 2 groups of 25 mice each using Vivo Manager® software (Biosystemes, Couternon, France). The mean body weight of both groups was not statistically different (analysis of variance).

2. Treatment Schedule

The mice from groups 1 to 5 received administrations of VXM04m-empty, the animals from groups 6 to 10 received administrations of VXM04m. Both VXM04m-empty and VXM04m were thawed and administered within 30 min, the working solutions were discarded after use. The treatment dose of VXM04m-empty and VXM04m was $10^{10}$ CFU in 100 µl per administration. VXM04m-empty and VXM04m were administered by oral gavage (per os, PO) via a cannula with a volume of 0.1 ml. Regardless of animal groups, each animal received pre-dose application buffer to neutralize acid in the stomach prior dosing (100 µl/animal/application). Thus buffer was composed by dissolution of 2.6 g sodium hydrogen carbonate, 1.7 g L-Ascorbic acid, 0.2 g lactose monohydrate in 100 ml of drinking water and was applied within 30 min prior application of VXM04m-empty and VXM04m. The treatment schedule was as follows:

The mice from groups 1 to 5 received daily PO administrations of VXM04m-empty at $10^{10}$ in CFU every two days for four consecutive times (Q2D×4).

The mice from groups 6 to 10 received daily PO administrations of VXM04m at $10^{10}$ in CFU every two days for four consecutive times (Q2D×4).

3. Animal Monitoring and Termination

The viability and behavior of the animals was recorded every day, body weights were measured twice a weak.

Irrespective of the administered *Salmonella* vaccine, mice were terminated after 5 (groups 1 and 6), 7 (groups 2 and 7), 10 (groups 3 and 8), 14 (groups 4 and 9) and 21 (groups 5 and 10) days post vaccination phase (5 mice per animal group and time point). Isoflurane (Baxter, France) was used to anaesthetize the animals before termination. Animals were terminated by cervical dislocation. An autopsy (macroscopic examination of heart, lungs, liver, spleen, kidneys and gastrointestinal tract) was performed on all terminated animals. At the time of mice termination, spleens were collected and placed individually into single ID labeled tubes containing chilled PBS (2-8° C.) each and stored over night at 2-8° C. Freshly isolated and purified splenocytes were used for Pentamer analysis. Freshly prepared CD8+ cells were used for ELISpot analysis.

4. Splenocyte Preparation

Splenocyte preparation was performed as follows: In a washing step a part of the PBS was discarded and replaced by fresh PBS. A 100 µm nylon Cell Strainer (BD Falcon) was hung into the opening of a 50 ml Falcon containing 5 ml 1×PBS. The spleens were cut with a scalpel and then pushed through the cell strainer with the stamp of a 5 ml syringe. One strainer was used per spleen, the strainer was always rinsed in between with sterile 1×PBS. The cells were centrifuged at 1,500 rpm (approximately 450 g) for 10 min at 2-8° C. and the supernatant was discarded. 1 ml ACK-Ery-Lysis buffer (8.3 g/l $NH_4$, 1 g/l $KHCO_3$, 0.037 g/l EDTA; pH 7.2-7.4) was added per spleen to lyse the red blood cells. The solution was incubated for 30 sec at RT. 10 ml of PBS were added and the cells were again spun down at 1,500 rpm for 10 min at 2-8° C., the supernatant was discarded. The pellet was resuspended in 10 ml DMEM media. Live/dead cell staining was performed with trypan blue and the cell number was counted. The cell suspension was split for the subsequent analyses. About one third was used for Pentamer analysis, the rest was used for the ELISpot analysis.

5. Pentamer Analysis

Pentamer Analysis included a viability staining and the Pentamer staining. For the viability staining, one vial of the fluorescent reactive dye (Pacific Orange—component A) and the vial of anhydrous DMSO (component B) were brought to room temperature before the caps were removed. 50 µl of DMSO (component B) was added to the vial of reactive dye (component A). Subsequently the well was mixed and it was confirmed visually that all of the dye had dissolved. The solution of reactive dye was used without delay, within a few hours of reconstitution. The suspension of cells containing at least $1 \times 10^6$ cells was centrifuged and the supernatant was discarded. The cells were washed once with 1 ml of PBS and resuspended in 1 ml of PBS. The cells were counted and the density was adjusted with PBS to $1 \times 10^6$ cells in a 1 ml volume. 1 µl of the reconstituted fluorescent reactive dye was added to 1 ml of the cell suspension. The suspension was then mixed thoroughly and incubated at room temperature for 30 min, protected from light. The cells were washed once with 1 ml of PBS with 1% Fetal Calf Serum (FCS) and resuspended in 1 ml of PBS with 1% FCS.

For Pentamer staining, splenocytes prelabelled with Pacific Orange for viability gating were used. The Pro5® Recombinant MHC Pentamers used are listed in the following Table 1:

| Pentamer description including sequence | Pentamer nomenclature | mMesothelin start position |
|---|---|---|
| Unlabelled Pro5 MHC Pentamer H-2Db GQKMNAQAI Mesothelin | MSLN-GAI-Penta | 406 |
| Unlabelled Pro5 MHC Pentamer H-2Kb ACAHFFSL Mesothelin | MSLN-ASL-Penta | 138 |
| Unlabelled Pro5 MHC Pentamer H-2Kb CSRSFLLL Mesothelin | MSLN-CLL-Penta | 18 |
| Unlabelled Pro5 MHC Pentamer H-2Kb GAADFASL Mesothelin | MSLN-GSL-Penta | 54 |
| Unlabelled Pro5 MHC Pentamer H-2Kb IPFTYEQL Mesothelin Pro5 Fluorotag R-PE | MSLN-IQL-Penta | 344 |

Pro5® Pentamers were centrifuged in chilled microcentrifuge at 14,000×g for 5-10 minutes to collect any protein aggregates present in the solution at the bottom of the vial in order to avoid non-specific staining. The supernatant was used for Pentamer staining. All reagents were maintained on ice, shielded form light, until required. $1 \times 10^6$ splenocytes were allocated per staining condition. The cells were washed with 2 ml wash buffer (PBS with 1% FCS) and spun down (500×g for 5 minutes), the supernatant was discarded and the cells were resuspended in the residual volume (~50 μl). The tubes were kept chilled on ice for all subsequent steps, except where otherwise indicated. One test (2 μl) of unlabeled Pentamer was added to the cells and the solution was mixed by pipetting and incubated at room temperature (22° C.) for 10 min, shielded from light. The cells were then washed with 2 ml wash buffer and resuspended in the residual liquid (~50 μl). Pro5® Fluorotag R-PE was spun in a chilled microcentrifuge at 14,000×g for 3 minutes to remove protein aggregates that would otherwise contribute to non-specific binding. The reagents were maintained on ice, shielded from light, until required. The supernatant was used for Pentamer staining. 8 μl Pro5® Fluorotag and 1 μl of anti-CD8 FITC and 0.5 μl anti-CD3 APC/Cy-7 antibodies were added and the solution was mixed by pipetting. The samples were incubated on ice for 20 minutes, shielded from light. The cells were washed twice with 2 ml wash buffer and each tube was mixed. 200 μl of fix solution (1% FCS, 2.5% formaldehyde in PBS) was added and the tubes were vortexed. Thorough vortexing was important to avoid cell clumping. The tubes were stored in the dark in the refrigerator until ready for data acquisition. In any case the samples were left for 3 hours before proceeding with data acquisition due to morphology changes after fixing.

Figure 4:
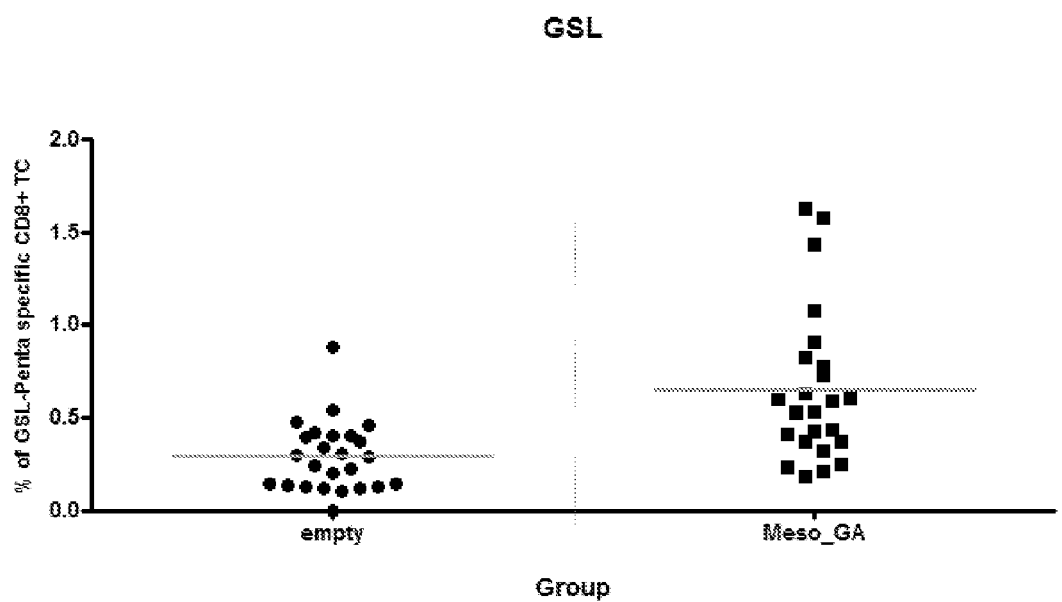

Specific binding to Pentamers each (manufactured by Proimmune) was investigated. Murine Mesothelin (mMesothelin) specific $CD8^+$ T cells were counted after selecting the appropriate gates. Ratios of mMesothelin specific $CD8^+$ T cells were calculated based on binding affinity to the Pentamers. The ratios were compared between VXMO4m and VXMO4m-empty control group and within groups over time. All statistical analyses were performed using VIVO MANAGER® software (Biosystems, Dijon, France). A p value <0.05 was considered significant. The individual percentages of Meso-specific CD8+ cells are presented in FIGS. 4-9. FIGS. 4 to 6 represent Meso-specific CD8+ cells detected by MSLN-GSL-Penta; FIGS. 7 to 9 represent Meso-specific CD8+ cells detected by MSLN-IQL-Penta. The Immune kinetics (mean values) peaked at 10 days post-vaccination. The percentage of Meso-specific CD8+ cells on day 10 was significantly increased compared to the control group, irrespective of the used Pentamers.

The invention claimed is:

1. A method for treating or vaccinating a patient against a cancer comprising administering to the patient an attenuated mutant strain of *Salmonella* comprising at least one copy of a recombinant DNA molecule comprising an expression cassette encoding Mesothelin (MSLN), wherein the MSLN is human MSLN, the attenuated mutant strain of *Salmonella* is *Salmonella typhi* Ty21a, and wherein the expression cassette is a eukaryotic expression cassette.

2. The method of claim 1, wherein the recombinant DNA molecule further comprises the kanamycin antibiotic resistance gene, the pMB1 ori, and wherein the eukaryotic expression cassette encoding human MSLN is under the control of a CMV promoter, wherein the human MSLN has the nucleic acid sequence as found in SEQ ID NO:2.

3. The method of claim 1, wherein the method further comprises administration of one or more further strain(s) of *Salmonella* comprising at least one copy of a recombinant DNA molecule comprising an expression cassette encoding a tumor antigen and/or a tumor stroma antigen, and wherein the one or more further strain(s) of *Salmonella* is/are *Salmonella typhi* Ty21a comprising a eukaryotic expression cassette.

4. The method of claim 3, wherein the one or more further strain(s) of *Salmonella typhi* Ty21a of claim 3, is co-administered with the attenuated mutant strain of *Salmonella typhi* Ty21a.

5. The method of claim 1, wherein the method further comprises administering chemotherapy, radiotherapy or a checkpoint inhibitory antibody to the patient.

6. The method of claim 1, wherein the attenuated mutant strain of *Salmonella typhi* Ty21a is administered orally.

7. The method of claim 1, wherein the cancer is selected from mesotheliomas, ovarian and pancreatic cancers, squamous cell carcinomas of the cervix, head and neck, vulva, lung and esophagus, lung adenocarcinomas, endometrial carcinomas, biphasic synovial sarcomas, desmoplastic small round cell tumors, and gastric adenocarcinomas.

8. The method of claim 1, wherein the single dose comprises from about $10^5$ to about $10^{11}$, particularly from about $10^6$ to about $10^{10}$, more particularly from about $10^6$ to about $10^9$, more particularly from about $10^6$ to about $10^8$, most particularly from about $10^6$ to about $10^7$ colony forming units (CFU) of said attenuated mutant strain of *Salmonella typhi* Ty21a.

9. The method of claim 1 further comprising the step of assessing the MSLN expression pattern and/or the pre-immune response against MSLN of the patient, and wherein the treatment is individualized cancer immunotherapy treatment.

10. The method of claim 1, wherein MSLN has the amino acid sequence of SEQ ID NO:1 or is at least 80% identical to SEQ ID NO:1.

11. The method of claim 3, wherein said one or more further strain(s) of *Salmonella typhi* Ty21a comprise(s) a strain of *Salmonella typhi* Ty21 encoding human VEGFR-2.

12. The method of claim 5, wherein the attenuated mutant strain of *Salmonella typhi* Ty21a is administered before or during the chemotherapy or the radiotherapy treatment, or before or during administration of the checkpoint inhibitory antibody or before and during the chemotherapy or the radiotherapy treatment or administration of the checkpoint inhibitory antibody.

* * * * *

UNITED STATES PATENT AND TRADEMARK OFFICE
CERTIFICATE OF CORRECTION

PATENT NO. : 10,441,645 B2
APPLICATION NO. : 15/785743
DATED : October 15, 2019
INVENTOR(S) : Marco Springer and Heinz Lubenau Page 1 of 1

It is certified that error appears in the above-identified patent and that said Letters Patent is hereby corrected as shown below:

In the Claims

In Claim 8, Column 24, Line 11, please delete "most particularly from about $10^6$ to about 10' colony forming" and insert --most particularly from about $10^6$ to about $10^7$ colony forming--

Signed and Sealed this
Thirty-first Day of December, 2019

Andrei Iancu
*Director of the United States Patent and Trademark Office*